United States Patent
Falco et al.

(10) Patent No.: US 8,249,317 B2
(45) Date of Patent: Aug. 21, 2012

(54) METHODS AND SYSTEMS FOR COMPENSATING FOR CHANGES IN ANATOMY OF RADIOTHERAPY PATIENTS

(75) Inventors: Tony Falco, La Prairie (CA); Martin Lachaine, Montreal (CA)

(73) Assignee: Eleckta Ltd., Montreal, Quebec (CA)

( * ) Notice: Subject to any disclaimer, the term of this patent is extended or adjusted under 35 U.S.C. 154(b) by 907 days.

(21) Appl. No.: 12/176,785

(22) Filed: Jul. 21, 2008

(65) Prior Publication Data

US 2009/0022383 A1 Jan. 22, 2009

Related U.S. Application Data

(60) Provisional application No. 60/951,005, filed on Jul. 20, 2007.

(51) Int. Cl.
G06K 9/00 (2006.01)
(52) U.S. Cl. ........................................................ 382/128
(58) Field of Classification Search .................. 382/128
See application file for complete search history.

(56) References Cited

U.S. PATENT DOCUMENTS

| | | |
|---|---|---|
| 3,082,322 A | 3/1963 | Koerner et al. |
| 3,777,124 A | 12/1973 | Pavkovich |
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,882,741 A | 11/1989 | Brown et al. |
| 4,923,459 A | 5/1990 | Nambu |
| 4,943,990 A | 7/1990 | Schar |
| 5,039,867 A | 8/1991 | Nishihara et al. |
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |

(Continued)

FOREIGN PATENT DOCUMENTS

CA 2416887 2/2002

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner* — Christopher Mahoney
(74) *Attorney, Agent, or Firm* — Goodwin Procter LLP

(57) ABSTRACT

Portal images are combined with 3D ultrasound to determine adjustments to patient treatment parameters. The images are acquired while the patient is in an initial position, and the images are registered to a treatment coordinate system. The images are combined and outlines of anatomical structures are superimposed on the portal images, resulting in new portal images that incorporate the anatomy extracted from the ultrasound. The enhanced portal images are used to identify modifications to the treatment parameters.

5 Claims, 4 Drawing Sheets

U.S. PATENT DOCUMENTS

| | | |
|---|---|---|
| 5,299,288 A | 3/1994 | Glassman et al. |
| 5,301,674 A | 4/1994 | Erikson et al. |
| 5,379,642 A | 1/1995 | Reckwerdt et al. |
| 5,389,101 A | 2/1995 | Heilbrun et al. |
| 5,391,139 A | 2/1995 | Edmundson |
| 5,397,329 A | 3/1995 | Allen |
| 5,408,101 A | 4/1995 | Wong |
| 5,411,026 A | 5/1995 | Carol |
| 5,438,991 A | 8/1995 | Yu et al. |
| 5,442,675 A | 8/1995 | Swerdloff et al. |
| 5,446,548 A | 8/1995 | Gerig et al. |
| 5,447,154 A | 9/1995 | Cinquin et al. |
| 5,483,961 A | 1/1996 | Kelly et al. |
| 5,511,549 A | 4/1996 | Legg et al. |
| 5,524,627 A | 6/1996 | Passi |
| 5,531,227 A | 7/1996 | Schneider |
| 5,531,520 A | 7/1996 | Grimson et al. |
| 5,553,618 A | 9/1996 | Suzuki et al. |
| 5,591,983 A | 1/1997 | Yao |
| 5,603,318 A | 2/1997 | Heilbrun et al. |
| 5,609,485 A | 3/1997 | Bergman et al. |
| 5,645,066 A | 7/1997 | Gandini et al. |
| 5,673,300 A | 9/1997 | Reckwerdt et al. |
| 5,690,108 A | 11/1997 | Chakeres |
| 5,715,166 A | 2/1998 | Besl et al. |
| 5,734,384 A | 3/1998 | Yanof et al. |
| 5,740,225 A | 4/1998 | Nabatame |
| 5,754,623 A | 5/1998 | Seki et al. |
| 5,757,881 A | 5/1998 | Hughes |
| 5,778,043 A | 7/1998 | Cosman |
| 5,810,007 A | 9/1998 | Holupka et al. |
| 5,836,954 A | 11/1998 | Heilbrun et al. |
| 5,851,183 A | 12/1998 | Bucholz |
| 5,859,891 A | 1/1999 | Hibbard |
| 5,871,445 A | 2/1999 | Bucholz |
| 5,952,577 A | 9/1999 | Passi |
| 5,991,703 A | 11/1999 | Kase |
| 6,019,724 A | 2/2000 | Gronningsaeter et al. |
| 6,038,283 A | 3/2000 | Carol et al. |
| 6,094,508 A | 7/2000 | Acharya et al. |
| 6,106,470 A | 8/2000 | Geiser et al. |
| 6,112,341 A | 9/2000 | Moreland |
| 6,117,081 A | 9/2000 | Jago et al. |
| 6,118,848 A | 9/2000 | Reiffel |
| 6,119,033 A | 9/2000 | Spigelman et al. |
| 6,122,341 A | 9/2000 | Butler et al. |
| 6,129,670 A | 10/2000 | Burdette et al. |
| 6,138,495 A | 10/2000 | Paltieli et al. |
| 6,144,875 A | 11/2000 | Schweikard et al. |
| 6,146,390 A | 11/2000 | Heilbrun et al. |
| 6,198,957 B1 | 3/2001 | Green |
| 6,208,883 B1 | 3/2001 | Holupka et al. |
| 6,259,943 B1 | 7/2001 | Cosman et al. |
| 6,269,143 B1 | 7/2001 | Tachibana |
| 6,285,805 B1 | 9/2001 | Gueziec |
| 6,292,578 B1 | 9/2001 | Kalvin |
| 6,307,914 B1 | 10/2001 | Kunieda et al. |
| 6,314,310 B1 | 11/2001 | Ben-Haim et al. |
| 6,325,758 B1 | 12/2001 | Carol et al. |
| 6,345,114 B1 | 2/2002 | Mackie et al. |
| 6,359,959 B1 | 3/2002 | Butler et al. |
| 6,366,798 B2 | 4/2002 | Green |
| 6,385,286 B1 | 5/2002 | Fitchard et al. |
| 6,385,288 B1 | 5/2002 | Kanematsu |
| 6,390,982 B1 | 5/2002 | Bova et al. |
| 6,405,072 B1 | 6/2002 | Cosman |
| 6,423,009 B1 | 7/2002 | Downey et al. |
| 6,438,202 B1 | 8/2002 | Olivera et al. |
| 6,459,769 B1 | 10/2002 | Cosman |
| 6,491,702 B2 | 12/2002 | Heilbrun et al. |
| 6,511,430 B1 | 1/2003 | Sherar et al. |
| 6,516,046 B1 | 2/2003 | Frohlich et al. |
| 6,535,574 B1 | 3/2003 | Collins et al. |
| 6,546,073 B1 | 4/2003 | Lee |
| 6,553,152 B1 | 4/2003 | Miller et al. |
| 6,560,311 B1 | 5/2003 | Shepard et al. |
| 6,567,684 B1 * | 5/2003 | Chenevert et al. ............ 600/410 |
| 6,585,651 B2 | 7/2003 | Nolte et al. |
| 6,591,127 B1 | 7/2003 | McKinnon |
| 6,600,810 B1 | 7/2003 | Hughes |
| 6,621,889 B1 | 9/2003 | Mostafavi |
| 6,628,983 B1 | 9/2003 | Gagnon |
| 6,631,284 B2 | 10/2003 | Nutt et al. |
| 6,636,622 B2 | 10/2003 | Mackie et al. |
| 6,641,539 B2 | 11/2003 | Hirooka et al. |
| 6,661,870 B2 | 12/2003 | Kapatoes et al. |
| 6,662,036 B2 | 12/2003 | Cosman |
| 6,669,635 B2 | 12/2003 | Kessman et al. |
| 6,683,985 B1 | 1/2004 | Kase et al. |
| 6,690,965 B1 | 2/2004 | Riaziat et al. |
| 6,714,627 B1 | 3/2004 | Brown et al. |
| 6,725,079 B2 | 4/2004 | Zuk et al. |
| 6,728,424 B1 | 4/2004 | Zhu et al. |
| 6,731,970 B2 | 5/2004 | Schlossbauer et al. |
| 6,750,873 B1 | 6/2004 | Bernardini et al. |
| 6,754,374 B1 | 6/2004 | Miller et al. |
| 6,785,409 B1 | 8/2004 | Suri |
| 6,804,548 B2 | 10/2004 | Takahashi et al. |
| 6,914,959 B2 | 7/2005 | Bailey et al. |
| 6,915,008 B2 | 7/2005 | Barman et al. |
| 6,968,224 B2 | 11/2005 | Kessman et al. |
| 6,980,679 B2 | 12/2005 | Jeung et al. |
| 7,092,109 B2 | 8/2006 | Satoh et al. |
| 7,095,823 B2 | 8/2006 | Topolnjak et al. |
| 7,260,426 B2 | 8/2007 | Schweikard et al. |
| 7,333,644 B2 | 2/2008 | Jerebko et al. |
| 7,343,030 B2 | 3/2008 | Sawyer |
| 7,430,321 B2 | 9/2008 | Okada et al. |
| 7,438,685 B2 | 10/2008 | Burdette et al. |
| 7,801,349 B2 | 9/2010 | Wang et al. |
| 2001/0035871 A1 | 11/2001 | Bieger et al. |
| 2001/0049475 A1 | 12/2001 | Bucholz et al. |
| 2002/0018588 A1 | 2/2002 | Kusch |
| 2002/0065461 A1 | 5/2002 | Cosman |
| 2002/0082494 A1 | 6/2002 | Balloni et al. |
| 2002/0087101 A1 | 7/2002 | Barrick et al. |
| 2002/0122530 A1 | 9/2002 | Erbel et al. |
| 2002/0156375 A1 | 10/2002 | Kessman et al. |
| 2002/0176541 A1 | 11/2002 | Schubert et al. |
| 2002/0183610 A1 | 12/2002 | Foley et al. |
| 2002/0188194 A1 | 12/2002 | Cosman |
| 2003/0018232 A1 | 1/2003 | Elliott et al. |
| 2003/0028401 A1 | 2/2003 | Kaufman et al. |
| 2003/0112922 A1 | 6/2003 | Burdette et al. |
| 2003/0144813 A1 | 7/2003 | Takemoto et al. |
| 2003/0153825 A1 | 8/2003 | Mooradian et al. |
| 2003/0182072 A1 | 9/2003 | Satoh et al. |
| 2003/0231790 A1 | 12/2003 | Bottema |
| 2004/0015075 A1 | 1/2004 | Kimchy et al. |
| 2004/0015176 A1 | 1/2004 | Cosman |
| 2004/0034301 A1 | 2/2004 | Falco |
| 2004/0092815 A1 | 5/2004 | Schweikard et al. |
| 2004/0146137 A1 | 7/2004 | Bruder et al. |
| 2004/0176925 A1 | 9/2004 | Satoh et al. |
| 2004/0184646 A1 | 9/2004 | Oosawa |
| 2004/0252870 A1 | 12/2004 | Reeves et al. |
| 2004/0260142 A1 | 12/2004 | Lovoi |
| 2005/0020917 A1 | 1/2005 | Scherch |
| 2005/0180544 A1 | 8/2005 | Sauer et al. |
| 2005/0251029 A1 | 11/2005 | Khamene et al. |
| 2006/0020195 A1 | 1/2006 | Falco et al. |
| 2006/0074292 A1 | 4/2006 | Thomson et al. |
| 2006/0093205 A1 | 5/2006 | Bryll et al. |
| 2006/0120608 A1 | 6/2006 | Luo et al. |
| 2006/0241443 A1 | 10/2006 | Whitmore et al. |
| 2006/0285641 A1 | 12/2006 | Scherch |
| 2006/0293583 A1 * | 12/2006 | Saracen et al. ............... 600/407 |
| 2007/0015991 A1 | 1/2007 | Fu et al. |
| 2007/0038058 A1 | 2/2007 | West et al. |
| 2007/0055090 A1 | 3/2007 | Neustadter et al. |
| 2008/0039713 A1 | 2/2008 | Thomson et al. |
| 2008/0064953 A1 | 3/2008 | Falco et al. |
| 2008/0219405 A1 | 9/2008 | Falco et al. |
| 2008/0292194 A1 | 11/2008 | Schmidt et al. |
| 2009/0003523 A1 | 1/2009 | Raanes et al. |

| | | | |
|---|---|---|---|
| 2009/0093716 | A1 | 4/2009 | Deischinger et al. |
| 2009/0110145 | A1 | 4/2009 | Lu et al. |
| 2011/0069815 | A1 | 3/2011 | Nord et al. |

FOREIGN PATENT DOCUMENTS

| | | |
|---|---|---|
| CA | 2621741 | 3/2007 |
| EP | 0647457 | 4/1995 |
| EP | 951697 | 10/1999 |
| EP | 1304960 | 5/2003 |
| EP | 1426806 | 6/2004 |
| EP | 1757228 | 2/2007 |
| FR | 2778574 | 11/1999 |
| JP | 2006000220 A | 1/2006 |
| WO | WO-9902074 | 1/1999 |
| WO | WO-99/06644 | 2/1999 |
| WO | WO-99/26534 | 6/1999 |
| WO | WO-99/27839 | 6/1999 |
| WO | WO-0105316 | 1/2001 |
| WO | WO-0209588 | 2/2002 |
| WO | WO-2003/039370 | 5/2003 |
| WO | WO-03/076003 | 9/2003 |
| WO | WO-2006051523 | 5/2006 |

OTHER PUBLICATIONS

Booth, *Modelling the impact of treatment uncertainties in radiotherapy*, University of Adelaide, Mar. 2002), Section 2.4 (<http://thesis.library.adelaide.edu.au/uploads/approved/adt-SUA20020816.175301/public/03chapter2.pdf>.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al., Three Dimensional Conformal External Beam Treatment of Prostate Cancer <http://prostate-help.org/download/pilgrim/10rad.pdf>.

Hanks et al., Clinical and Biochemical Evidence of Control of Prostate Cancer at 5 Years After External Beam Radiation, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing,, pp. 196-213 (1992).

Krempien et al., Daily patient set-up control in radiation therapy by coded light projection, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) <http://www.phoenix5.org/Infolink/Michalski/#3>.

Paskalev et al., Daily Target Localization for Prostate Patients based on 3-D Image Correlation, Phys. Med. Biol., vol. 49, pp. 931-939 (2004).

Pennec et al,. A Framework for Uncertainty and Validation of 3-D Registration Methods Based on Points and Frames, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., Conventional vs. Conformal Radiotherapy for Prostate Cancer: Preliminary Results of Dosimetry and Acute Toxicity, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-671 (2000).

Robinson, *Advances in Multi-Modal Data Analysis: The ANALYZE Software Environment*, <http://www.ii.metu.edu.tr/~med-ii/makaleler/analyze_sw_enve.pdf>, 5 pages. Downloaded on Aug. 10, 2004.

Soffen E.M. et al. Conformal static field radiation therapy treatment of early prostate cancer versus non-conformal techniques: A reduction in acute morbidity. Int J Radiat Oncol Biol Phys, 24: 485-488 (1992).

Thayananthan, A. et al., <http://mi.eng.cam.ac.uk/~bdrs2/papers/thayananthan_cvpr03.pdf>, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Zhang, Iterative Point Matching for Registration of Free-Form Curves and Surfaces, International Journal of Computer Vision, 13(2):119-152 (1994).

<http://www.ucsf.edu/jpouliot/Course/chapter5.htm>.
<http://www.acmp.org/meetings/hershey_2001/highlights/benedict.pdf>.
<http://www.ucsf.edu/jpouliot/Course/Lesson22.htm>.
<http://www.gemedicalsystems.com/patient/see_treat/positioning.html>.
<http://www.emoryradiationoncology.org/high-technology.htm>.
<http://www.varian.com/pinf/imr000c.html>.
<http://www.ucsf.edu/jpouliot/Course/conformal_radiation_therapy.htm>.

Written Opinion of the International Search report for PCT/CA2005/001105 dated Oct. 27, 2005.

International Search Report for PCT/CA2005/01105 dated Oct. 27, 2005.

International Search Report for PCT/CA2005/001106 dated Nov. 15, 2005.

Written Opinion for PCT/CA2005/001106 dated Nov. 15, 2005.

International Preliminary Report on Patentability for International Application No. PCT/CA2005/001106 dated Jan. 23, 2007.

Written Opinion of the International Searching Authority for International Application No. PCT/CA2005/001106 dated Oct. 25, 2005.

International Search Report for PCT/CA2007/001626 dated Jan. 3, 2008 (4 pages).

Written Opinion of the International Searching Authority for PCT/CA2007/001626 dated Dec. 21, 2007 (7 pages).

International Preliminary Report on Patentability for PCT/CA2005/001428 dated Oct. 3, 2007 (1 page).

Written Opinion of the International Searching Authority for PCT/CA2005/001428 dated Nov. 8, 2005 (6 pages).

International Search Report for PCT/CA2007/000898 dated Jul. 12, 2007 (3 pages).

Written Opinion of the International Searching Authority for PCT/CA2007/000898 dated Jul. 23, 2007 (6 pages).

International Search Report for PCT/CA2006/001289 dated Oct. 30, 2006 (3 pages).

Written Opinion of the International Searching Authority for PCT/CA2006/001289 dated Oct. 30, 2006 (6 pages).

Written Opinion of the International Searching Authority for PCT/CA2006/001461 dated Dec. 8, 2006 (5 pages).

International Search Report for PCT/CA2006/001461 dated Nov. 30, 2006 (5 pages).

Aoki, Y. et al. An Integrated Radiotherapy Treatment System and its Clinical Application, Radiation Medicine, vol. 5, No. 4, pp. 131-141, 1987.

Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.

Bijhold, J. et al. Fast evaluation of patient set-up during radiotherapy by aligning features in portal and simulator images, Phys. Med. Biol., 1999, vol. 36, No. 12, pp. 1665-1679.

Bijhold, J. Three-dimensional verification of patient placement during radiotherapy using portal images, Med. Phys. 20 (2), Pt. 1, Mar./Apr. 1993. pp. 347-356.

Boctor, et al., A Rapid Calibration Method for Registration and 3D Tracking of Ultrasound Images Using Spatial Localizer, Proceedings of the SPIE (2003).

Boyer, A. A review of electronic portal imaging devices (EPIDs), Med. Phys. 19 (1), Jan./Feb. 1992 pp. 1.

Brunie L. et al. Pre-and intra-irradiation multimodal image registration: principles and first experiments, Radiotherapy and Oncology 29 (1993) pp. 244-252.

Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (4 pages).

Claim Chart for Claim 10 of US Patent No. 5,447,154.

Cuadra, M.B. et al., Atlas-based Segmentation of pathological MR brain images using a model of lesion growth; Medical Imaging IEEE Transactions on, vol. 23, No. 10, pp. 1301-1314, Oct. 2004.

Cuisenaire, O., <http://www.tele.uci.ac.be/PEOPLE/OC/these/node74.html,>Posted Oct. 5, 1999, Downloaded from the Internet on Aug. 10, 2004.

Cuisenaire, O., <http://www.tele.ucl.ac.be/PEOPLE/OC/these/node75.html,>Posted Oct. 5, 1999, Downloaded from the Internet on Aug. 10, 2004.

Czarnota G.J. et al. Ultrasound imaging of apoptosis: high-resolution non-invasive monitoring of programmed cell death in vitro, in situ and in vivo, British Journal of Cancer (1999) 81(3), pp. 520-527.

International Search Report and Written Opinion for PCT/CA2009/000750, mailed Sep. 18, 2009 (8 pages).

International Search Report for PCT/CA2005/001428 dated Nov. 16, 2005.

Le Verre, C. et al. Intensity-Based Registration of Portal Images for Patient Positioning in Radiotherapy, 2005.

Leszczynski K W et al., "An Image Registration scheme applied to verification of radiation therapy" British Journal of Radiology British Inst. Radiol UK [Online] vol. 71, No. 844, Apr. 1998, ISSN: 0007-1285, retrieved from the Internet: url:http://bjr.birjournals.org/cgi/reprint/71/844/413.pdf. [retrieved on Nov. 10, 2009].

Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.

Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).

Meertens, H. et al. A method for the measurement of field placement errors in digital portal images, Phys. Med. Biol., 1990, vol. 35, No. 3, pp. 299-323.

Mencarelli, et al., "A Dosimetric Method to derive optimal couch corrections in the presence of anatomical deformations for H & N cancer," abstract, 2011, 2 pages.

Nagel, et al., "Online dose-guided setup correction protocol for hypo fractionated lung radiotherapy," abstract, 2009, 1 page.

Reinstein, L. et al. Radiotherapy Portal Imaging Quality, Report of AAPM Task Group No. 28, American Association of Physicists in Medicine by the American Institute of Physics, New York, 1988.

Search Report for European Patent Application No. 06790638.8, mailed Apr. 23, 2010 (7 pages).

Simpson, R.G. et al. A 4-MV CT scanner for radiation therapy: The prototype system. Med. Phys. 9(4), Jul./Aug. 1982, pp. 574-579.

Supplementary European Search Report dated Oct. 25, 2010 by Examiner Pau Montes (5 pages).

Supplementary European Search Report dated Oct. 30, 2008 for European Patent Application No. 05788508.9/PCT/CA2005001428.

Supplementary European Search Report for PCT/CA2005001106_RNM-003PC_dated Nov. 10, 2009, 6 pages.

Supplementary European Search Report, for PCT Application No. PCT/CA2005001135, dated Feb. 27, 2009 (12 pages).

Supplementary Partial European Search Report for EP Application No. 5763463, dated Nov. 30, 2009, 7 pages.

Swindell, W. et al. Computed tomography with a linear accelerator with radiotheraphy applications, Med. Phys. 10(4), Jul./Aug. 1983, pp. 416-420.

Troccaz, J. et al. Conformal external radiotherapy of prostatic carcinoma: requirements and experimental results, Radiotherapy and Oncology 29 (1993) pp. 176-183.

Troccaz., J et al. Patient Setup Optimization for External Conformal Radiotherapy, Journal of Image Guided Surgery, 1, pp. 113-120 (1995).

Van de Geijn, J. et al. A Graticule for Evaluation of Megavolt X Ray Port Films, Radiation Oncology Biology Physics, Nov. 1982, vol. 8, No. 11 pp. 1999-2000.

Zitova, B. et al., Image Registration Methods: A survey, Image and Vision Computing, Elsevier, Guildford, GB, vol. 21, No. 11, Oct. 1, 2003 (24 pages).

Holupka, et al., (1996), "Ultrasound Image Fusion for External Beam Radiotherapy for Prostate Cancer," *J. Radiation Oncology Biol. Phys.*, vol. 35, No. 5, pp. 975-984.

Search Report for European Application No. 08783253.1 mailed Dec. 30, 2011 (7 pages).

* cited by examiner ns and systems for compensating for changes in anatomy of radiotherapy patients

CROSS-REFERENCE TO RELATED APPLICATIONS

This application claims priority to and the benefit of U.S. provisional patent application Ser. No. 60/951,005, filed Jul. 20, 2007, the disclosure of which is incorporated herein by reference in its entirety.

TECHNICAL FIELD

This invention relates to methods and systems for using imaging to guide radiotherapy treatments.

BACKGROUND INFORMATION

Radiation therapy relies on devising a treatment plan, which includes the arrangement of therapeutic radiation beams, patient positioning relative to the beams, beam energies, apertures, and doses, and other factors. Typically, the treatment plan is based on a three-dimensional (3D) computed tomography (CT) dataset acquired prior to the first treatment session. Although CT scans provide a good physical map of electron density within the patient, they also have limitations. For example, CT scans are devoid of functional information about tumors and provide poor soft-tissue contrast for some organs. To circumvent these limitations, other secondary images may also be acquired, using modalities such as positron-emission tomography (PET), magnetic resonance imaging (MRI) or ultrasound. PET, for example, gives functional information about tumor metabolism, and MRI and ultrasound give superior soft-tissue contrast for some organs.

After the treatment plan is developed, the patient is positioned in the treatment room using external skin markings and radiation is delivered according to the treatment plan. This is typically repeated for a number of sessions, for example, once a day for 30 sessions. During this time period, however, a patient's internal anatomy may change. For example, it is known that the prostate can change positions significantly depending on rectal and bladder filling. In an attempt to provide more accurate delivery of radiation therapy, image-guided radiotherapy (IGRT) has become more common. Using IGRT, an image is acquired prior to each session and used to correct the treatment plan for anatomical changes. In principle, a completely new treatment plan can be generated prior to each treatment session—a technique known as adaptive radiotherapy (ART). Although effective, ART is not generally undertaken because re-planning is time-consuming and must be validated and approved for each session. Instead, current clinical practice commonly corrects for physiological changes by shifting the patient (using the treatment couch, for example) in order to best align the target anatomy to the planned location. This is accomplished by comparing the target structure position to its position on a reference image acquired during planning.

One common technique for implementing IGRT is portal imaging, i.e., using the treatment beam to acquire images with either film or a two-dimensional (2D) electronic portal imaging detector (EPID). Due to the high energy (megavolt range) of the treatment beam, image quality is generally inferior to diagnostic (kilovolt range) x-ray images, and provides little or no soft-tissue contrast. Portal images can be effective, however, for localization of bony anatomy, air pockets, and imaging skin surface. One advantage to using the IGRT approach is that the information is inherently acquired by and related to the treatment beam. To ensure the treatment position is correct relative to bony anatomy, the portal images are compared to digitally reconstructed radiographs (DRRs), which are the reconstruction of a 2D projection radiograph from a given beam direction, calculated from the planning CT dataset. EPIDs have been developed not only for electronic record-keeping, but also to make the acquisition more rapid, and to allow online corrections to patient position prior to each treatment fraction. Further, the introduction of flat-panel detectors has improved image quality of EPIDs such that it is comparable to conventional film-based imaging.

Software has been developed to enable rapid displacement calculations using localization images. Typically, 2D structures, called overlays, are extracted from CT contours and displayed on the DRRs on a console. EPID images are acquired from (typically) two angles, such as anterior-posterior and lateral, and the DRR overlays are shown superimposed on the port films. The operator then moves the overlays such that they fit the anatomy as seen on the EPIDs, and the amount of shift is calculated. This allows the therapist to displace the couch to compensate for any discrepancies.

Since portal images do not show soft-tissue contrast, one practice facilitating IGRT is to implant, in the treated organ (e.g., prostate), gold seeds that may be identified on the portal images. By comparing these positions to those on the planning CT, shifts can be executed to correct for organ motion. The use of seeds is invasive, however, and the resulting images do not give a complete picture of the organ and surrounding anatomy.

Another approach includes placing a conventional or cone-beam CT scanner in the treatment room. These scanners generate 3D images, and can either be of diagnostic quality or can use the high-energy treatment beam to produce the 3D images (referred to as megavoltage CT). These images provide a good geometric image of the patient, are similar in nature to the planning CT, and have some soft-tissue contrast which can be used to perform IGRT. For some sites such as prostate, however, fiducial marker seeds are typically used because the soft-tissue contrast is still unacceptable.

Ultrasound has also been used for IGRT, as it provides good soft-tissue contrast. Two or more ultrasound images are referenced to a 3D coordinate system, and are either used individually or are reconstructed to a full 3D image dataset. Patient displacements can then be determined from the ultrasound images. Although they can provide excellent soft-tissue contrast for organs such as the prostate, uterus or breast tumor cavities and do not require fiducial markers, ultrasound images do not give bony anatomy, or a complete anatomical image of the patient.

There has been research and development into the use of in-treatment-room MRI and PET for IGRT, but technical hurdles remain before this technology becomes commercially available.

SUMMARY OF THE INVENTION

The present invention provides systems and methods for improving imaging for IGRT. Embodiments of the invention rely on the integration and use of multiple modalities in the treatment room, registered to a common coordinate system, in order to modify treatment parameters.

In one aspect, the invention combines portal images and 3D ultrasound to determine a patient shift to be applied during radiotherapy treatment. A set of baseline radiotherapy treatment parameters are established, and, during therapy, two or more registered images of the area under treatment are taken, with at least some of the images being portal images taken from at least one beam direction, and at least one of the images being a non-x-ray-based 3D image. The images are then registered to a coordinate system associated with a treatment device. The non-x-ray-based 3D image is segmented to form a 3D surface, which is projected onto the plane of each portal image, thereby enhancing the portal images with data from the projected surface. The baseline treatment parameters are then updated based on the registered images. In this fashion, new portal images are produced which incorporate the anatomy extracted from the ultrasound.

In another aspect a system for identifying changes to patient treatment parameters during delivery of radiotherapy includes a first and second register and a processor. The first register stores a set of baseline treatment parameters, and the second register stores the images of an anatomical region to be treated. The images are obtained using different imaging modalities, such that at least some of the images are portal images from at least one beam direction, and at least one of the images is a non-x-ray-based 3D image. The processor is configured to register the images to a coordinate system associated with a treatment device, segment the non-x-ray-based 3D image to form a 3D surface, project the surface onto the plane of each portal image, enhance the portal images with data from the projected surface, and determine modifications to the baseline treatment parameters based on the registered images.

The present invention is not limited to the above applications, but encompasses the use of more than one image in the treatment room, registering these two or more images, and using anatomy from at least two of the images to modify treatment parameters.

BRIEF DESCRIPTION OF THE DRAWINGS

In the drawings, like reference characters generally refer to the same parts throughout the different views. Also, the drawings are not necessarily to scale, emphasis instead is generally being placed upon illustrating the principles of the invention.

DETAILED DESCRIPTION

Figure 1:
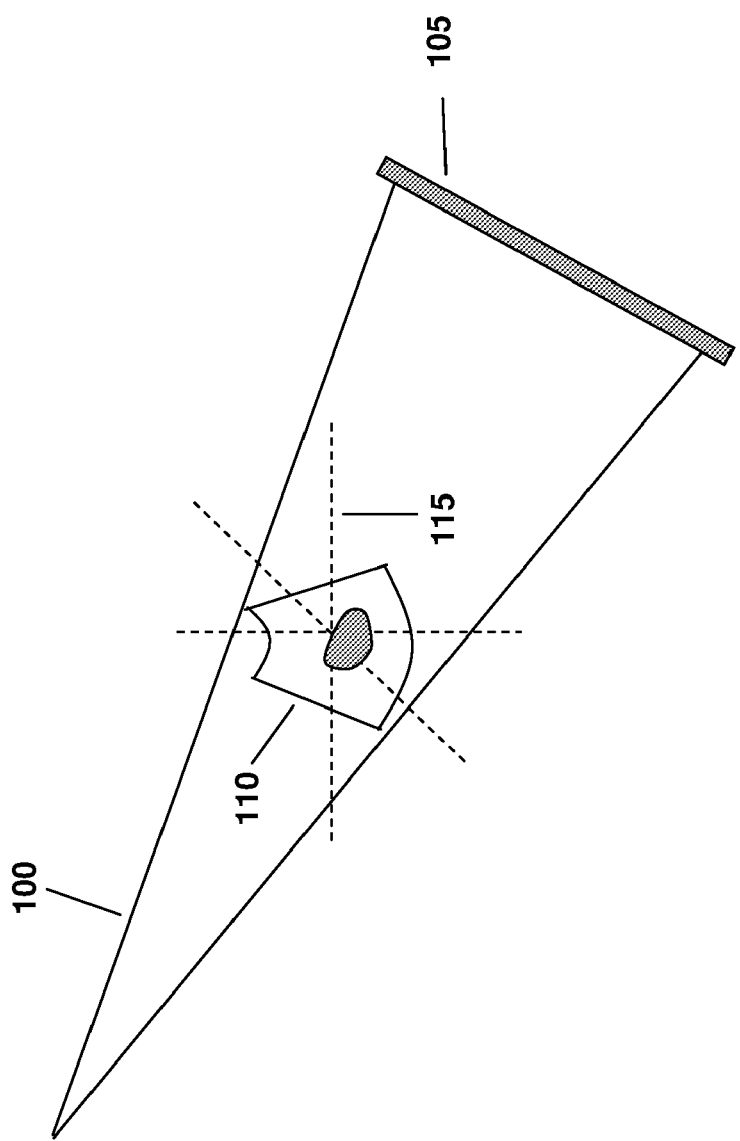
FIG. 1 schematically shows the combination of a 3D ultrasound image and a portal image.

In FIG. 1, which illustrates an embodiment of the invention, the beam 100 of a linear accelerator (not shown), at a known gantry angle, is used in combination with a portal imager 105 to form a 2D image of the patient. The gantry angle may then be changed, and another image acquired. Typically at least two images are acquired from different directions using the portal imager 105. The portal imager 105 is preferably an EPID, producing digital images using the treatment beam 100. The portal images may be stored in a computer. A 3D ultrasound image 110 is also acquired, before or after the portal images but within as close a time frame as possible so that the patient does not move significantly. The portal and ultrasound images may be calibrated to a common coordinate system 115 whose origin coincides with the mechanical isocenter of the linear accelerator. This coordinate system 115 may be identified using perpendicular lasers passing through the origin. Systems and methods for calibrating 3D ultrasound images to such as coordinate system are known in the art.

Still referring to FIG. 1, relevant anatomy in the 3D ultrasound image is contoured (either manually or using an automatic segmentation algorithm) to form one or more 3D surfaces, each corresponding to a separate anatomical region. For example, the bladder and prostate can be contoured separately, even though they may appear in the same image set. The surface(s) are then projected onto the 2D portal images in the direction of the beam (i.e., along a beam's eye view).

Figure 2:
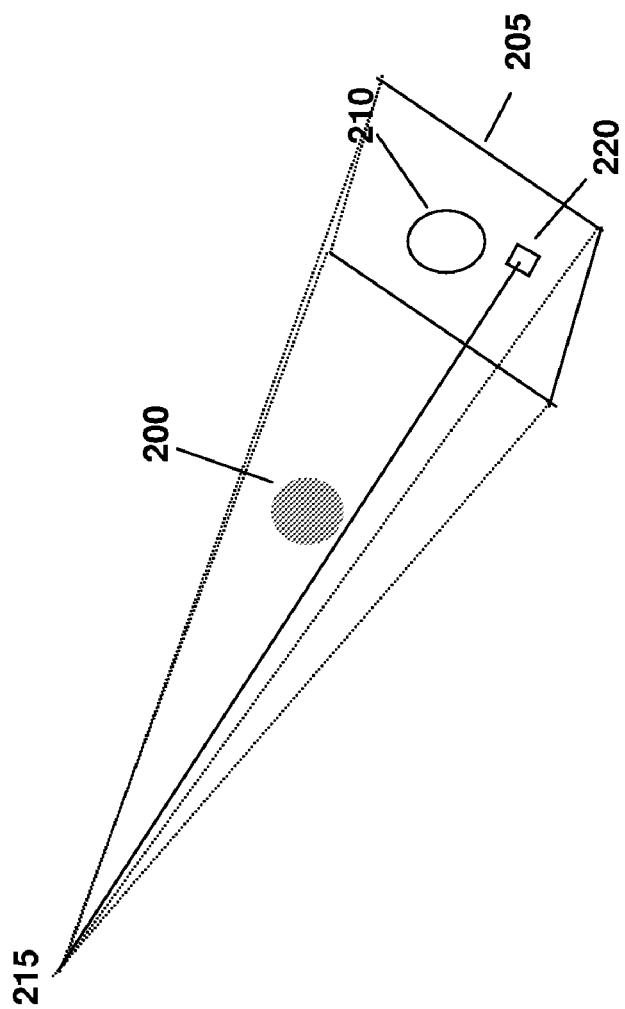
FIG. 2 schematically shows the creation of a 2D projection contour onto a portal image, created from a 3D surface of an organ obtained from a 3D ultrasound image.

In particular, from a given angle corresponding to a single portal image, a 3D surface can be projected into the portal-image by various methods. Referring to FIG. 2, a 3D surface 200 is projected onto the 2D image plane 205 (which coincides with the portal and ultrasound images) to produce a 2D surface projection outline 210. This can be done, for example, by tracing a ray from the beam source 215 to a given pixel 220 in the image 205. If the ray passes through the surface 200, then the pixel 220 is considered within the projection outline 210, otherwise it is considered outside the outline. This procedure may be repeated for all the pixels (or a reasonable subset consistent with resolution requirements) of the image 205. The filled pixels then represent the projection 210 of the surface 200. The outline of the filled pixels can be extracted and the projection contour 210 outlined.

In some cases, adjustments to various imaging parameters may be needed to correctly calibrate the 3D surface 200 to the image plane 205. For example, the scale of the portal image may require modification, the center of the portal image may need to be moved relative to the source 215, and/or rotations of the image may be needed relative to the room coordinate system 115. In principle, all images may be scaled such that distances are measured in relation to the isocenter of the linear accelerator, i.e., the origin of the room coordinate system 115. Accordingly, knowing the pixel size of the portal image is not enough, since the distance between the plane of the portal imaging detector (the medium on which the portal image is recorded) and the origin of the room coordinate system affects the scaling for a particular image. The image calibration parameters can be calculated by detector calibration, image pre-calibration or image self-calibration.

For detector calibration, the imaging detector is itself calibrated such that its parameters are known. For example, since the physical pixel size of the detector elements is known, and the image receptor can be calibrated to be at a known physical distance from the beam source, the scaling at isocenter may be readily computed. If the distance from the source changes, the pixels can be scaled to account for the new distance. The center pixel of the detector is also calibrated to be at a known offset from the central axis of the beam—either the offset is permanently fixed or the detector electronics can determine an offset value. The rotation of the detector is accurately fixed such that it is always aligned with the room coordinate system. Even with frequent detector calibration, there are likely to be deviations from ideal and drifts over time, thus requiring further calibration.

To assist with calibration of the detector prior to imaging, an object (or "phantom") of known geometry may be imaged with the detector. In some embodiments, the phantom is a plate having an arrangement of some number (e.g., four) radio-opaque markers at known distances relative to the center of the plate. An image of the plate is acquired using the portal imaging device, and the markers identified on the image. The relationship of the markers on the image relative to their known positions on the phantom can be used to calculate the calibration parameters. In principle, each gantry angle has its own calibration parameters, since, for example, the detector may sag as the gantry is rotated. As a result, the central axis of the beam may not always pass exactly through the same point as the gantry is rotated, and therefore the calibration parameters should be checked periodically to identify any drift.

For image self-calibration, the outline of the radiation field is detected and the outline edges are compared to the expected beam aperture, which may be rectangular or, in some instances, an irregular shape extracted from the treatment plan. Comparing the expected shapes to the detected shapes, the calibration parameters can be determined for the image. One advantage of this approach is that the state of the detector is known relative to the room coordinate system, i.e., the detector can be moved in any configuration and an accurate calibration can still be computed.

Other approaches can also be used to calibrate the portal images, such as using a graticule (a radio-opaque grid placed in the head of the linear accelerator), which appears in the portal image. Furthermore, instead of using portal images, similar 2D images may acquired using diagnostic-energy x-ray tubes mounted in the treatment room.

Figure 3:
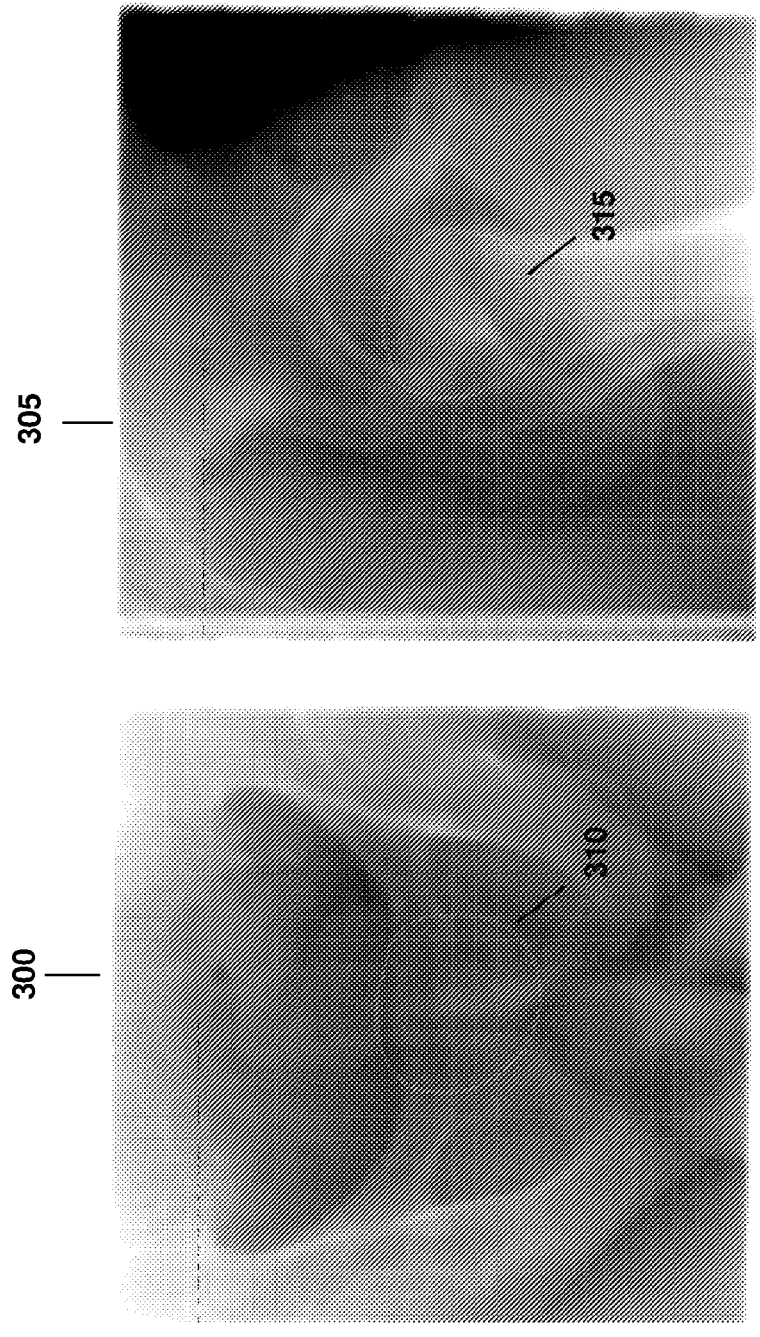
FIG. 3 shows portal images enhanced in accordance with the present invention.

With the ability to project the surface contour onto a calibrated portal image, each acquired portal image can be enhanced by augmenting it with an image of the soft-tissue anatomy extracted from the 3D ultrasound scan, as shown in the portal images of FIG. 3. Image 300 was acquired at an anterio-posterior beam direction, while the image 305 was acquired with a lateral beam direction. The prostate is not visible in either, but the bony anatomy of the pelvis is clearly visible. The prostate surface, as contoured on ultrasound images, is projected as a white line superimposed on the portal images, as indicated at 310 and 315.

The ultrasound-enhanced portal images, once created, can be used to calculate patient shifts or other changes in treatment parameters, thereby permitting treatment delivery to account for changes in anatomy that deviate from the plan.

Portal images are typically compared to digitally DRRs. These are simulated projections through the CT dataset, from the planned beam angles (or other more convenient angles), to form 2D images for each beam. By observing differences between the portal images and the DRRs, the treatment couch can be shifted to improve patient alignment with the beam(s). If the portal images have been enhanced using the above methods, the DRR may also be enhanced using ultrasound imaging. If, for example, a 3D ultrasound image is acquired during the planning CT session (e.g., as described in co-pending patent application Ser. No. 10/343,336, which is incorporated in its entirety herein by reference), the contours obtained from the ultrasound image can be projected onto the DRRs, thereby allowing for direct comparison between ultrasound-enhanced portal images and ultrasound-enhanced DRRs. Enhancing a DRR with the ultrasound contour obtained at time of simulation is done in the same fashion as described above with respect to the enhancement of portal images, except typically the DRRs need not be calibrated since their geometric parameters are typically known.

While the invention has been described particularly in relation to using both portal images and ultrasound for IGRT, the invention also extends to matching the coordinate systems of any two or more imaging modalities, and using images obtained using these modalities to modify treatment parameters. For example, CT and ultrasound images can be acquired in succession prior to a patient treatment; each is calibrated to the room coordinates of the linear accelerator. The ultrasound-derived anatomical contours may then be superimposed onto the CT image and the treatment parameters modified to better align with anatomy imaged by both modalities. For example, the bladder, rectum and bony anatomy can be identified on the CT, while the prostate can be better identified on the ultrasound. In other instances, one or more organs can be identified on images obtained using both modalities, but some organ edges are better revealed by one modality than by the other. After the anatomy is identified using the multimodality images, beam shapes, angles, energies, patient position, etc. can be modified to account for the observed anatomy, which may differ from the planning anatomy.

Figure 4:
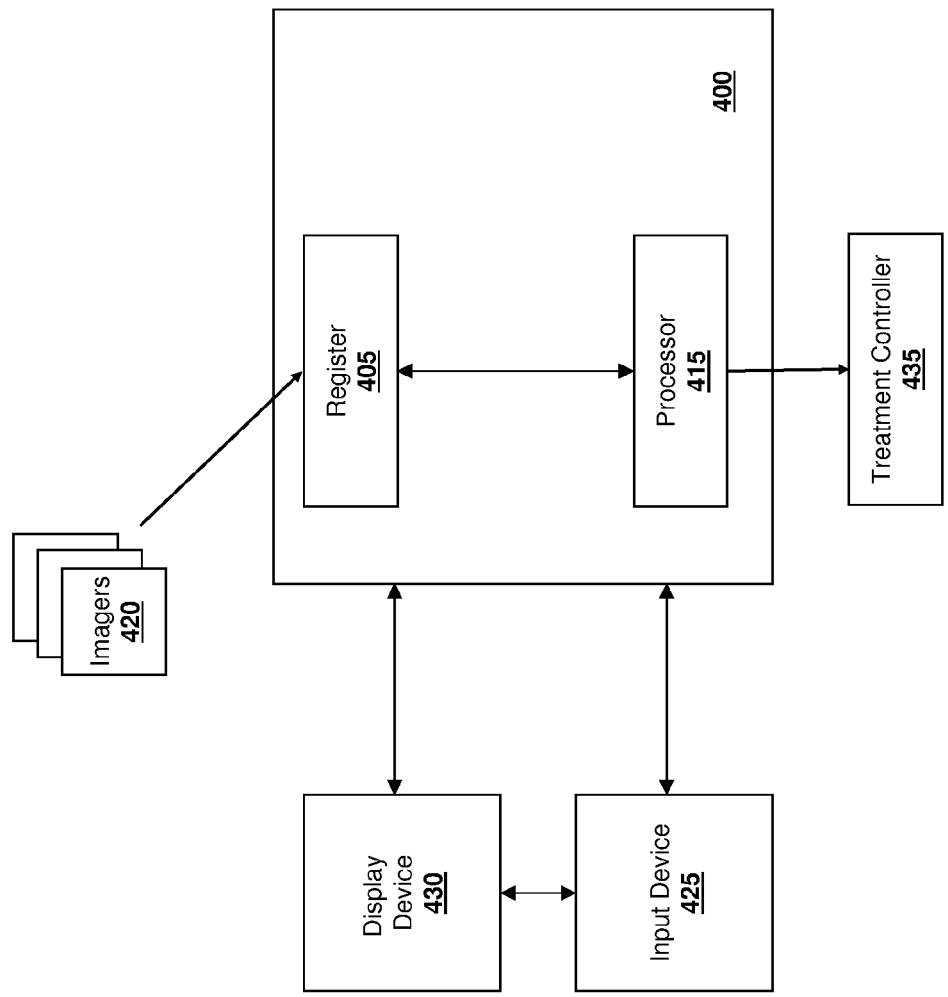
FIG. 4 schematically illustrates a system in accordance with an embodiment of the present invention.

FIG. 4 schematically depicts a hardware embodiment of the invention realized as a system 400 for modifying treatment parameters based on multimodal images. The system 400 comprises a register 405 and a processor 415.

The register 405, which may be any suitably organized data storage facility (e.g., partitions in RAM, etc.), receives images from a plurality of imagers, collectively indicated at 420, which reflect different imaging modalities. Imagers 420 may include one or more of an MRI, CT/PET scanner, ultrasound device, or x-ray device. In some embodiments, the images are stored on a data-storage device separate from the imager (e.g., a database, microfiche, etc.) and sent to the system 400. The register 405 may receive the images through conventional data ports and may also include circuitry for receiving analog image data and analog-to-digital conversion circuitry for digitizing the image data.

The register 405 provides the images to the processor 415, which implements the functionality of the present invention in hardware or software, or a combination of both on a general-purpose computer. In particular, processor 415 registers the images and creates an enhanced image, which may be displayed on a device 430. The processor 415 thereupon computes patient shifts or other changes in treatment parameters, which are communicated to the controller 435 of a treatment device such as a linear accelerator. The controller 435, in turn, causes appropriate adjustments to be made based on the modified treatment parameters.

Alternatively or in addition, a user, via an input device 425, may influence, approve, override or revise the modifications to the treatment parameters based on his or her review of the composite image on device 430.

The programming for processor 415 may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of modifying treatment parameters for a patient undergoing radiotherapy, the method comprising the steps of:
- (a) establishing a set of baseline treatment parameters during a treatment planning session prior to a treatment delivery session;
- (b) during the treatment delivery session obtaining, using different imaging modalities, at least two registered images of an anatomical region to be treated wherein at least some of the images are portal images from at least one beam direction, and at least one of the images is a non-x-ray-based 3D image;
- (c) registering the at least two images to a coordinate system associated with a treatment device;
- (d) segmenting the non-x-ray-based 3D image to form a 3D surface;
- (e) projecting the surface onto the plane of each portal image;
- (f) enhancing the portal images with data from the projected surface, wherein the enhancing comprises identifying one or more anatomical regions based on the portal images, identifying one or more different anatomical regions based on the projected surface other than those identified based on the portal images, and superimposing the identified different anatomical regions onto the portal images; and
- (g) modifying the baseline treatment parameters based on the enhanced portal images.

2. The method of claim 1 further comprising:
enhancing one or more digitally reconstructed images with data from the projected surface; and
modifying the baseline treatment parameters based on a comparison between the enhanced portal images and the enhanced digitally reconstructed images.

3. A system for identifying changes to patient treatment parameters, the system comprising:
- (a) a first register for storing a set of baseline treatment parameters obtained during a treatment planning session prior to a treatment delivery session;
- (b) a second register for storing at least two images of an anatomical region to be treated, each image being obtained during the treatment delivery session using different imaging modalities wherein at least some of the images are portal images from at least one beam direction, and at least one of the images is a non-x-ray-based 3D image; and
- (c) a processor configured to retrieve and execute stored computer programming instructions to:
  - (i) register the at least two images to a coordinate system associated with a treatment device;
  - (ii) segment the non-x-ray-based 3D image to form a 3D surface;
  - (iii) project the surface onto the plane of each portal image;
  - (iv) enhance the portal images with data from the projected surface, wherein the enhancing comprises identifying one or more anatomical regions based on the portal images, identifying one or more different anatomical regions based on the projected surface other than those identified based on the portal images, and superimposing the identified different anatomical regions onto the portal images; and
  - (ii) determine modifications to the baseline treatment parameters based on the enhanced portal images.

4. The system of claim 3 further comprising a controller for affecting the modifications based on the modified treatment parameters.

5. The system of claim 3 wherein the modifications comprise positional changes to the patient.

* * * * *